US006007691A

United States Patent [19]
Klock, Jr.

[11] Patent Number: 6,007,691
[45] Date of Patent: Dec. 28, 1999

[54] FLUOROPHORE ASSISTED CARBOHYDRATE ELECTROPHORESIS DIAGNOSIS

[75] Inventor: John C. Klock, Jr., Nicasio, Calif.

[73] Assignee: Glyko, Inc., Novato, Calif.

[21] Appl. No.: 08/052,785

[22] Filed: Apr. 23, 1993

Related U.S. Application Data

[63] Continuation-in-part of application No. 07/696,584, May 7, 1991, Pat. No. 5,205,917.

[51] Int. Cl.$^6$ .......................... G01N 27/26; G01N 27/447
[52] U.S. Cl. .......................... 204/612; 204/456; 204/461; 204/606
[58] Field of Search .......................... 204/180.1, 299 R, 204/182.8, 456, 461, 466, 467, 468, 469, 606, 612, 616, 618

[56] References Cited

U.S. PATENT DOCUMENTS

| | | | |
|---|---|---|---|
| 4,705,616 | 11/1987 | Andresen et al. | 204/452 |
| 4,852,137 | 7/1989 | Mackay | 378/62 |
| 4,874,492 | 10/1989 | Mackay | 204/461 |
| 4,975,165 | 12/1990 | Brandley | 204/461 |
| 5,019,231 | 5/1991 | Brandley et al. | 204/461 |
| 5,035,786 | 7/1991 | Brandley et al. | 204/461 |
| 5,104,508 | 4/1992 | Williams et al. | 204/461 |

FOREIGN PATENT DOCUMENTS

WO 92/11531   7/1992   WIPO.

OTHER PUBLICATIONS

Noboru Tomiya et al "Structural Analysis of N–Linked Oligosaccharides by a Combination of Glycopeptidase, Exoglycosidases, and High–Performance Liquid Chromatography" Analytical Biochemistry 163 (Jun. 1987) 489–499.

Chandra Prakash et al, "A New Fluorescent Tag for Labeling of Saccharides" Analytical Biochemistry, vol. 128, No. 1 (Jan. 1983) 41–46.

Supplemental European Search Report, Jun. 29, 1993, EPX.

Martinez, J., et al., "The Role of Sialic Acid in the Dysfibrinogenemia Associated With Liver Disease: Distribution of Sialic Acid on the Constituent Chains," *Blood*, 61:1196–202 (1983) No month available.

Parekh, R.B., et al., "Association of rheumatoid arthritis and primary osteoarthritis with changes in the glycosylation pattern of total serum IgG," *Nature*, 316:452–457 (1985) No month available.

Winter, G. and Milstein, C., "Man–made antibodies," *Nature* 349:293–299 (1991) No month available.

Lorincz, A.E., et al., "The Early Laboratory Diagnosis of Mucopolysaccharidoses," *Ann. Clin. Lab. Sci.*, 12:258–266 (1982) No month available.

Rademacher, T.W., et al., "Glycobiology," *Ann. Rev. Biochem.*, 57:785–838 (1988) No month available.

Sewell, A.C., et al., "Comprehensive Urinary Screening for Inborn Errors of Complex Carbohydrate Metabolism," *Klin Wochenschr*, 57:581–585 (1979) No month available.

Jackson, P., "The use of polyacrylamide–gel electrophoresis for the high–resolution separation of reducing saccharides labelled with the fluorophore 8–aminohapthalene–1, 3,6–trisulphonic acid," Biochem.J. 270:705–713 (1990) No month available.

*Primary Examiner*—Robert Warden
*Assistant Examiner*—John S. Starsiak, Jr.
*Attorney, Agent, or Firm*—Albert P. Halluin; Howrey & Simon

[57] ABSTRACT

The subject invention provides methods and kits for conveniently diagnosing various physiological conditions that produce altered levels of specific carbohydrates, known as diagnostic carbohydrates. Measurement of the levels of the diagnostic carbohydrates is performed by fluorophore assisted carbohydrate electrophoresis. Physiological conditions of particular interest that may be ascertained by the subject invention include carbohydrate metabolism diseases, autoimmune diseases, neoplasia, toxic chemical exposure and microbial infections. Fluorophore assisted carbohydrate electrophoresis diagnosis may be applied to various patient specimens, including blood, urine and skin.

14 Claims, No Drawings

FLUOROPHORE ASSISTED CARBOHYDRATE ELECTROPHORESIS DIAGNOSIS

CROSS REFERENCE TO RELATED APPLICATION

This application is a continuation in part of application Ser. No. 07/696,584 filed May 7, 1991 now U.S. Pat. No. 5,205,917.

INVENTOR: John C. Klock, Jr.

FIELD OF THE INVENTION

The subject invention is in the field of medical diagnostics, in particular diagnostics based on changes in carbohydrate composition.

BACKGROUND OF THE INVENTION

Carbohydrates play a number of extremely important roles in the functioning of living organisms. In addition to their metabolic and storage roles, carbohydrates are covalently attached to numerous other molecules such as proteins and lipids. Molecules such as glycoproteins and glycolipids are generally referred to as glycoconjugates. The biological importance of the carbohydrate portion of glycoconjugates can be seen, for example, in the role they play in affect the ability of glycoproteins to perform their biological functions, including such functions as ligand or receptor recognition.

As a consequence of their diverse and important biological functions, aberrations in the synthesis, degradation, or modification of carbohydrates may give rise to several diseases. Similarly many disease may alter the body's physiology so as to give rise to altered carbohydrate metabolism or the improper glycosylation of proteins, lipids and other glycoconjugates in the body.

Many of the biologically active carbohydrates in the body are polysaccharides and oligosaccharides that are produced in a variety of related forms rather than having a single defined structure. These families of related carbohydrates are frequently found to be components of the same glycoprotein. These families of glycoproteins that share the same polypeptide structure, but display variation in the glycosylation pattern have been referred to as glycoforms, Rademacher, et al, *Ann. Rev. Biochem.*, 57:789–838 (1988).

The relative abundance of members of glycoform family members have been shown to vary in accordance with certain disease states. For example, the disfibrinogenemia associated with liver disease has been associated with variations in the glycosylation of fibrinogens, Martinez, J., et al, *Blood,* 61:1196–202 (1983), and rheumatoid arthritis has been associated with changes in glycosylation of IgG, Parekh et al, *Nature,* 316:452–457 (1985).

Diseases based on improper metabolism of carbohydrates from glycoconjugates are well known. The general category of diseases is known by a variety of names, including lysosomal storage disorders, heteroglycanoses, inborn errors of complex carbohydrate metabolism, mucopolysaccharidoses and others. Each of these diseases is the result of a genetic inability to produce one or more of the enzymes required for the stepwise degradation of glycoproteins, mucopolysaccharides or glycolipids, or the carbohydrate portion of said glycoconjugates.

When one of these enzymes in the degradation pathway is incorrectly produced or missing completely, the molecule produced in the last working step of the degradation pathway accumulates due to the body's inability to further cleave the molecule. Over time, the compound that cannot be degraded accumulates to such an extent that it impedes normal biological function in a wide variety of cells throughout the body.

The consequences of this type of genetic defect vary among the different enzyme deficiencies, but the symptoms of these diseases may include organomegaly, corneal opacities, skeletal abnormalities and progressive mental retardation.

The diagnosis of these carbohydrate metabolism disorders has historically been difficult because few methods exist for the separation, detection and identification of a wide variety of complex carbohydrates. The two main methods that have been employed are carbohydrate staining techniques and chromatographic separation and detection methods.

The carbohydrates staining techniques, including the Berry Spot Test and the dimethylmethylene blue (DMB) assay rely on a specific reaction between a chemical dye and a specific class of oligosaccharides. The major application of these methods have been with the mucopolysaccharidoses, which are disorders of glycosaminoglycan degradation. These tests have been proposed for large scale screening, but they are limited to the specific disorders for which the chemistry is designed, and the tests have had a problem with a large number of false positive diagnoses. Sewell, et al, *Klin Wochenschr,* 57:581–585 (1979), or Lurincz, et al, *Ann. Clin. Lab. Sci.,* 12:258–266 (1982).

Chromatographic separation of oligosaccharides from glycoconjugates has also been proposed as a screening technique for these diseases, but there is no one chromatographic technique or set of chromatographic conditions that will facilitate the separation of the range of carbohydrate-based compounds that accumulate in all of these diseases. The techniques that have been developed include thin layer chromatography (TLC), high performance liquid chromatography and gas chromatography. Each of these methods has some utility in the diagnosis of the carbohydrate metabolic diseases, but they have found limited acceptance in clinical laboratories as a result of their limitations and/or complexity.

Thus it is of interest to provide a general technique for the diagnosis of a variety of diseases characterized by altered levels of carbohydrates in which the diagnostic technique does not require an a priori detailed knowledge of the structure of the carbohydrates.

SUMMARY OF THE INVENTION

The present invention is directed to methods and kits for the diagnosis of a variety of diseases or predispositions to disease that are characterized by altered levels of specific carbohydrates in the tissues of patients afflicted by the condition of interest.

The method of the subject invention involves the fluorescent labeling and electrophoretic separation of carbohydrate mixtures, followed by the measurement of the amount of specific carbohydrates in the original mixtures. By comparing the quantity of specific carbohydrates, i.e., diagnostic carbohydrates, present in patient samples for analysis with the diagnostic carbohydrate level present in an individual without the disease of interest, a variety of disease conditions may be diagnosed. Another aspect of the subject invention is the diagnosis of carriers of genetic diseases. Disease conditions capable of being diagnosed by the subject invention include carbohydrate metabolism disease, auto-immune diseases, infectious disease, exposure to toxic chemicals, and cancer. The subject invention may be used on samples obtained from humans or animals preferably, mammals. Another aspect of the invention is to provide for the early detection of diseases in infants. A diagnostic standard may be included in the electrophoretic separation.

In a preferred embodiment of the invention, the pattern of labeled carbohydrate bands produced by the electrophoretic separation is visualized using an imaging system based on a charge-coupled device (CCD) camera. Information from the CCD camera may subsequently be stored in digital form and analyzed by various computer programs for comparing diagnostic carbohydrate pattern between individuals and between reference standards. Additionally the gel separated diagnostic carbohydrates may be transferred to an immobilizing membrane, i.e., blotted and then probed with various diagnostic carbohydrate-specific reagents. Another aspect of the subject invention is the pretreatment of sample by a variety of procedures such as centrifugation, ultrafiltration solubilization, glycosidase, or glycosyl transferases treatment so as to provide for more readily interpretable results.

Another aspect of the invention is to provide methods for the diagnosis of diseases that may be characterized by altered levels of diagnostic carbohydrates where the method employs the step of treating patient samples, or portions of patient samples, with carbohydrate-modifying enzymes capable of using diagnostic carbohydrates as substrates. By looking for the changes in banding patterns (as determined by fluorophore-assisted carbohydrate electrophoresis) attributable to the activity of the enzyme, the diagnosis of various diseases may either be established or confirmed.

DESCRIPTION OF THE SPECIFIC EMBODIMENTS

The subject invention provides for the convenient diagnosis of a number of human and animal diseases. By diagnosis of a disease, it is intended not simply the identification of a disease that has manifested symptoms, but also the identification of a variety of adverse physiological conditions, including the physiological conditions of individuals that have a propensity to develop a disease, i.e., prognostic uses, the identification of individuals possessing the genetic capacity to transmit a disease to descendants, and the identification of individual exposures to toxic chemicals. Furthermore, for the purpose of this application, the term "disease", when used non-specifically, includes those physiological conditions that are capable of being identified by diagnosis. Individuals manifesting a disease for diagnosis are defined to be "afflicted" individuals. The terms "individual" or "patient" include animals, especially mammals, in addition to humans.

The term "carbohydrate-modifying enzyme" as used herein refers to enzymes that can catalyze a chemical reaction wherein at least one of the reactants is a carbohydrate. It will be appreciated by the person of average skill in the art of biochemistry or organic chemistry that catalysts capable of catalyzing carbohydrate-modifying reactions that are not carbohydrate enzymes may, in certain circumstances be used in place of carbohydrate modifying enzymes. These other catalyst may include lectins, antibodies (abzymes), organic and inorganic catalysts, and a variety of proteins not traditionally considered enzymes but capable of acting similarly to enzymes, e.g., lactalbumin in lactose synthesis. The term "enzymes" as used herein refers to carbohydrate-modifying enzymes, unless indicated otherwise. Carbohydrate-modifying enzymes may alter the structure of the substrate carbohydrates in a variety of ways, including the reverse hydrolysis of linkages between saccharide units (transglycosidation by hydrolases), the formation of new linkages between saccharide units by glycosyltransferases, and the addition of various side groups to carbohydrate molecules. Carbohydrate-modifying enzymes include hydrolases, lyases, acetylases, sulfatases, phosphatases, kinases, epimerases, methylases, amidases, transferases, and the like. Carbohydrate-modifying enzymes are said to have a "carbohydrate-modifying activity." The term "carbohydrate-modifying activity" refers to the reactions catalyzed by the carbohydrate-modifying enzyme of interest.

A principal feature of the subject invention is the measurement of the levels of diagnostic carbohydrates present in a sample isolated from an individual suspected of being afflicted. The term "carbohydrate" includes carbohydrates alone, and glycoconjugates such as glycoproteins, glycolipids, proteoglycans, and the like. The term "diagnostic carbohydrate" is defined as carbohydrates that are altered in concentration in an afflicted individual as, compared with an unafflicted individual, wherein the difference in carbohydrate level is associated with the disease of interest in the afflicted individual.

Diagnostic carbohydrates may be covalently joined to polypeptides or lipids, or may be independent of other molecules. Diagnostic carbohydrates may be monosaccharides, oligosccharide, or polysaccharides. Diagnostic carbohydrates may be branched or unbranched. Diagnostic carbohydrates in a sample from an afflicted individual are present in a concentration that is either higher or lower than diagnostic carbohydrates present in a sample from an unafflicted individual. The term "higher" includes the presence of carbohydrates that are present as opposed to completely absent; similarly, the term "lower" includes the absence of carbohydrates as opposed to present in some quantity. The differences in diagnostic carbohydrate concentrations between afflicted and unafflicted individuals does not necessarily exist in all body tissues.

More than one diagnostic carbohydrate may be associated with a particular disease. Furthermore, when more than one diagnostic carbohydrate is associated with a given disease state, the levels of the different diagnostic carbohydrates may vary in concentration such the concentration levels of at least one of the diagnostic carbohydrates may be increased and the concentration levels of other diagnostic carbohydrates may be decreased in correlation with the presence and progression of the disease.

The concentration of diagnostic carbohydrates in a sample is measured by fluorophore assisted carbohydrate electrophoresis. Moreover, fluorophore assisted carbohydrate electrophoresis may be used to detect and quantitatively compare the amount of specific carbohydrates from a wide variety of specimens, including not only patient specimens for diagnosis, but to detect carbohydrate differences in plant extracts, food preparations, cosmetics, and bodily fluid or tissue specimens that are associated with specific non-disease associated genes, e.g. blood group types. The fluorophore assisted carbohydrate electrophoresis technique is described in detail in U.S. Pat. Nos. 4,874,492 and 5,104, 508, which are herein incorporated by reference. Fluorophore assisted carbohydrate electrophoresis permits the electrophoretic separation of a complex mixture of carbohydrates into distinct bands on a gel. Prior to electrophoresis, a carbohydrate mixture for analysis is treated with a fluorophore label that combines with the reducing end of the carbohydrates for analysis. The fluorophore label permits the quantitative measurement of the labeled carbohydrates by fluorescence. The fluorophore label either is charged or coupled with a charge imparting species when the fluorophore itself is uncharged. Thus the label not only fluorescently tags the carbohydrates, but imparts an ionic charge, permitting hitherto uncharged carbohydrates to migrate in an electric field. Suitable fluorescent labels include 8-aminonapthalene-1,3,6-trisulphonic acid (ANTS), 1-amino-4-napthalene sulfonic acid (ANSA), 1-amino-6, 8-disulphonic acid (ANDA), lucifer yellow, and 2-aminoacridone. A description of fluorophores suitable for use in the subject invention can be found in U.S. Pat. No. 5,035,786 and UK application GB/90/01448 filed Sep. 20, 1990 and published as PCT application WO 91/05256, which are herein incorporated by reference.

After the carbohydrates have been labeled, the sample is subsequently subjected to polyacrylamide gel electrophoresis, or similar electrophoresis separation means, in order to separate and concentrate the labeled carbohydrates into bands. The separated carbohydrates may be visualized directly by photoelectric menus fluorescence under U.V. light and the banding patterns stored photographically. Alternatively the separated carbohydrates may be visualized by photoelectric means, including laser-scanner photomultiplier tube systems and cooled charge coupled devices (CCD). CCD's are semiconductor imaging devices that permit the sensitive detection of emitted light. CCDs and their uses are described in U.S. Pat. Nos. 4,874,492 and 4,852,137 which are herein incorporated by reference. The image produced by the CCD may be subsequently transferred to a computer wherein the bands may be analyzed with respect to intensity, mobility, standards, and the like.

When performing fluorophore assisted carbohydrate electrophoresis diagnosis, electrophoretic separation should take place to an extent sufficient to independently resolve bands of diagnostic carbohydrates specific for the disease of interest. Electrophoresis may proceed past the point where some carbohydrates have been removed from the electrophoresis separation medium. Electrophoresis may be in one or in two dimensions. Two-dimensional separation of carbohydrates by fluorophore assisted carbohydrate electrophoresis is described in U.S. Pat. No. 4,975,165, which is herein incorporated by reference.

Fluorophore assisted carbohydrate electrophoresis diagnosis permits the diagnosis of a variety of diseases that produce alterations in the levels of diagnostic carbohydrates associated with the disease. A significant advantage of fluorophore assisted carbohydrate electrophoresis diagnosis is that diseases manifesting themselves through changes in diagnostic carbohydrate levels may be identified without a prior knowledge of the structure of the diagnostic carbohydrates of interest.

Of particular interest is the diagnosis of carbohydrate metabolic diseases. Carbohydrate metabolism diseases may be attributable to the inability to either produce or degrade specific carbohydrate structures. As a consequence of this inability, various diagnostic carbohydrates may be present in abnormal quantities in various tissues of afflicted individuals.

In addition to determining the presence of a disease, fluorophore assisted carbohydrate electrophoresis diagnosis may be used to monitor the treatment of diseases through alterations in the quantities of diagnostic carbohydrates observed as treatment progresses. Similarly, the progression of a disease may be monitored through fluorophore assisted carbohydrate electrophoresis diagnosis. Alterations in diagnostic carbohydrate levels may also be observed by screening for disease in individuals that have not yet displayed adverse symptoms. Of particular interest is prenatal and neonatal screening.

Many carbohydrate metabolic diseases are attributable, at least in part, to various genetic mutations. Individuals that carry genes encoding carbohydrate metabolic defects may be detected as a consequence of the diagnostic carbohydrate levels in their tissues, even though the affected individuals display no adverse symptoms. Fluorophore assisted carbohydrate electrophoresis diagnosis of genetically linked diseases provides significant advantages over conventional techniques for identifying individuals containing mutations of interest. These advantages include the lack of a need to isolate the mutant gene responsible for the disease, and freedom from the use of cumbersome nucleic acid hybridization technologies. Furthermore, fluorophore assisted carbohydrate electrophoresis is sufficiently sensitive that it may detect diagnostic carbohydrates present in quantities insufficient to produce symptoms.

Many inherited carbohydrate metabolic diseases, especially lysosomal storage diseases, have been discovered. These diseases include Hurler disease (MPS IH, i.e., mucopolysaccharidosis type IH), Scheie disease (MPS IS), Hurler-Scheie disease (MPS I H/S), Hunter disease (MPS II), Sanfilippo disease (MPS III), Morquio disease (MPS IV), Maroteaux-Lamy disease (MPS VI), Sly disease (MPS VIII), mannosidosis, fucosidosis, sialidosis, asparylglycosaminuria, Gaucher disease (glucosylceramide lipidosis), and Krabbe disease (galactoceramide-lipidosis), Fabry disease, Schindler disease, $GM_1$ gangliosidoses, $GM_2$ gangliosidoses, Tay-Sachs disease, Sandhoff disease, and mucolipidoses.

It will be appreciated that the subject invention may be used to diagnose diseases or genetic defects that are not yet known to manifest themselves through characterized changes in diagnostic carbohydrate composition. The utility of fluorophore assisted carbohydrate electrophoresis diagnosis for such diseases or genetic defects may be determined by using fluorophore assisted carbohydrate electrophoresis to compare the carbohydrate composition of samples between patients known to have the disease or genetic defect of interest and control subjects. Correlations between various disease states and diagnostic carbohydrate patterns may be established through well-recognized statistical techniques. Particularly preferred diseases for determination by fluorophore assisted carbohydrate electrophoresis diagnosis are diseases in which the disease is a consequence of characterized by errors in carbohydrate metabolism or in the protein glycosylation process.

Fluorophore assisted carbohydrate electrophoresis diagnosis may also be used to detect many diseases other than carbohydrate metabolic diseases. Other diseases that may be detected by fluorophore assisted carbohydrate electrophoresis diagnosis include cancer, organ-specific diseases such as liver or bone marrow disease and various auto-immune diseases.

Many tumor cells contain glycoproteins with unique carbohydrate structures that may be used as diagnostic carbohydrates. Tumor diagnostic carbohydrates of interest may be either membrane bound or secreted. In addition to indicating that a cell is cancerous, alteration in glycosylation may correlate with the metastatic potential of the cell. Many changes in the glycosylation of proteins have been shown to be associated with tumors; a review of these changes can be found in Rademacher, et al., *Ann. Rev. Biochem.* 57:785–838 (1988). Thus the presence of tumor cells may be detected by using fluorophore assisted carbohydrate electrophoresis diagnosis.

In addition to its use in detecting carbohydrate metabolic disorders, fluorophore assisted carbohydrate electrophoresis diagnosis may be used to detect and identify infectious disease organisms. Many infectious organisms, including bacteria, fungi, and viruses, and multicellular parasites possess carbohydrates not normally found in the body tissue in which the organisms dwell. Fluorophore assisted carbohydrate electrophoresis diagnosis may be applied to detect the presence of pathogenic microorganisms in the body by screening and issue specimens for diagnostic carbohydrate structures produced by the infectious organisms of interest.

Samples for analysis by fluorophore assisted carbohydrate electrophoresis diagnosis may be prepared from many tissues or bodily fluids removed from subjects. Tissues or bodily fluids for analysis necessarily contain at least one diagnostic carbohydrate associated with the condition of interest. Suitable tissues or bodily fluids for analysis include, blood, saliva, urine, skin, muscle, bone marrow, cerebrospinal fluid, synovial fluid, lymphatic fluid, amniotic fluid and the like. Preferred tissues or bodily fluids for analysis are those tissues conveniently obtained from patients, particularly preferred tissues include urine and blood. The selection of tissues for use in the subject invention vary in accordance with the disease of interest being analyzed. Factors affecting the choice of tissues for analysis include: the quantity of diagnostic carbohydrates present in the sample, the quantity of background carbohydrates in the sample, and the presence of molecules in the sample capable of interfering with electrophoretic separation of the diagnostic carbohydrates.

Samples for analysis may require processing prior to the separation and quantification of the diagnostic carbohydrates by fluorophore assisted carbohydrate electrophoresis. The precise method of sample processing employed for a given test may vary in accordance with a number of factors attributable to the choice of sample tissue and the identity of the diagnostic carbohydrates; these factors include: the concentration of the diagnostic carbohydrate, the concentration of background carbohydrates, the presence of interfering molecules, i.e., molecules that adversely affect diagnostic carbohydrate band mobility or the fluorescent labeling of the diagnostic carbohydrates, and whether the diagnostic carbohydrates are bound to cells whether the carbohydrates are free or bound to other molecules, and the like. Suitable methods for processing samples include: dialysis, to remove interfering molecules; ultrafiltration, to concentrate diagnostic carbohydrates and remove interfering molecules; centrifugation, to remove interfering particulates or concentrate cells; precipitation, to remove interfering molecules; and detergent solubilization, to release diagnostic carbohydrates from cells.

After the diagnostic carbohydrates have been separated by fluorophore assisted carbohydrate electrophoresis, the carbohydrate may be subsequently transferred in situ on to a immobilizing matrix such as a nitrocellulose of nylon membrane by electroblotting or the like. Membranes containing the immobilized diagnostic carbohydrates (as well as other carbohydrates in the original mixture) may subsequently by probed with antibodies or similar specific binding reagents so as to indicate the presence and quantity of carbohydrates of interest. The transfer of fluorophore assisted carbohydrate electrophoresis separated carbohydrate onto immobilizing matrices is described in detail in U.S. Pat. No. 5,019,231, which is herein incorporated by reference.

It may be advantageous to modify the structure of some diagnostic carbohydrates by means of cleavage between carbohydrate subunits prior to electrophoretic separation. Suitable methods of cleavage include the use of carbohydrate-modifying enzymes that are glycosylytic enzymes, either endoglycosidases or exoglycosidases. Reasons for glycosidase treatment of samples include the liberation of diagnostic carbohydrates from glycoconjugates and the generation of new diagnostic carbohydrates that have a more convenient gel migration rate, i.e., better separation from non-diagnostic carbohydrates. Similarly, it may be advantageous to use glycosyl transferases along with a donor sugar, if required to produce a more convenient migration rate.

Another advantage of enzymatically modifying the structure of a diagnostic carbohydrate in a patient sample, either before or after fluorophore labeling, is to confirm the presence of the diagnostic carbohydrate associated with the disease state of interest. Thus the diagnosis of a disease may be established or confirmed by adding a carbohydrate-modifying enzyme capable of catalyzing a chemical reaction that structurally modifies a diagnostic carbohydrate present in a patient suffering from a disease of interest. Therefore, another embodiment of the subject invention is to divide samples for anylsis into various portions and add various carbohydrate-modifying enzymes to the differnt sample portions, where the substrates for the carbohydrate-modifying enzymes are diagnostic carbohydrates suspected of being in the sample for analysis; the various enzyme treated and untreated sample portions may then be separated, preferably by fluorphore assisted carbohydrate electrophoresis, and analyzed for differences in the diagnostic carbohydrate levels present in the various portions. For example, urine samples from a patient suffering from fucosidosis and a normal individual produce substantially different banding patterns when analyzed by fluorophore assisted carbohydrate electrophoresis. Incubating the fucosidosis patient sample with fucosidase (a substrate-specific carbohydrate-modifying enzyme) substantially alters the fluorophore assisted carbohydrate electrophoresis produced banding pattern, thus confirming a diagnosis of fucosidosis.

It may be of interest to employ specific binding reagents such as lectins or antibodies and the like (for a description of available antibody derivatives, see, Winter and Milstein, *Nature,* 349:293–299 (1991)). When analyzing the diagnostic carbohydrates, especially diagnostic carbohydrates that are components of glycoconjugates. The use of specific binding reagents may concentrate and purify diagnostic carbohydrates of interest so as to provide for more readily interpretable fluorophore assisted carbohydrate electrophoresis diagnosis results. For example, antibodies specific for the polypeptide portion of a glycoprotein with many glycoforms, but present in a tissue with a high carbohydrate background, may be used to immunoprecipitate the glycoprotein, the precipitated glycoprotein may then be subjected to endoglycosylase treatment to release the carbohydrate moieties prior to performing fluorophore assisted carbohydrate electrophoresis. The purified glycoforms could thus be easily interpreted in the presence of a reduced background.

In a preferred embodiment of the invention, diagnostic standards are included on the gels used to analyze the diagnostic carbohydrates in the subject samples; however, the information embodied by the diagnostic standard, e.g., band migration distance and intensity, may also be obtained from comparison with stored records made from diagnostic standards previously subjected to fluorophore assisted carbohydrate electrophoresis under conditions similar to the conditions the samples for analysis are exposed. Diagnostic standards may be both positive, i.e., corresponding to the complete carbohydrate pattern in an afflicted individual, or negative, i.e., corresponding to unafflicted individual. Diagnostic standards may have a composition similar to that of samples for analysis in that they may contain both diagnostic carbohydrates and background carbohydrates with composition similar to that found in actual samples. Diagnostic standards may be derived from samples obtained from afflicted and non-afflicted individuals. Alternatively, diagnostic standards may contain one or more diagnostic carbohydrates free of background carbohydrates.

Diagnostics standards may be labeled prior to the labeling of the samples for analysis; however diagnostic standards are preferably labeled concomitantly with the labeling for the standards for analysis. Furthermore, the diagnostic carbohydrates in the standards are preferably quantitated so as to provide for quantitative or qualitative comparisons with the amount diagnostic carbohydrates in the samples for analysis.

The subject invention also includes kits for performing fluorophore assisted carbohydrate electrophoresis diagnosis. Fluorophore assisted carbohydrate electrophoresis diagnosis kits provide collections of reagents required for performing fluorophore assisted carbohydrate electrophoresis diagnosis. Suitable kits enable laboratories to conveniently perform fluorophore assisted carbohydrate electrophoresis diagnosis. Kits may include reagents for performing tests to identify one or more specific disease states. Kits may include diagnostic standards, fluorescent label, blotting and binding materials, e.g., membranes, carbohydrate specific binding reagents, instructions, sample containers, and polyacrylamide gel reagents, precast gels, enzyme buffers, reducing agents (for use in the fluorophore labelling of carbohydrates), and enzymes cabable of catalyzing reactions that structurally altering diagnostic carbohydrates. More complete kits may include equipment for performing fluorophore assisted carbohydrate electrophoresis, such as polyacrylamide gel apparatus, CCDs, computers, software, and the like. Reagents included in fluorophore assisted carbohydrate electrophoresis diagnosis kits are preferably provided in premeasured amounts. The kits preferably include the instructions for carrying out the fluorophore assisted carbohydrate electrophoresis method of the present invention.

In a preferred embodiment of the subject invention, carbohydrate band data from the gels used to separate and quantitate diagnostic carbohydrates are read by means at a CCD and stored in a computer usable form. The image detected by the CCD, or other detection system, may be analyzed by image analysis software such as Optimas™ (Bioscan™) or similar image analysis programs. The data may be subjected to analysis by a variety of software programs. Software programs of interest include those with the ability to quantitate band intensity, measure band mobility, determine the relative molecular weight of carbohydrates forming bands, compare the standards with the samples for analysis, remove unwanted background information, and perform various forms of statistical analysis. In a preferred embodiment of the subject invention, quantitative data obtained from the fluorophore assisted carbohydrate electrophoresis is manipulated and/or presented in electronic spreadsheet form, e.g., Lotus 1-2-3™, Microsoft Excel™. It is also of interest to compile a computer database of fluorophore assisted carbohydrate electrophoresis banding patterns produced from patients known to suffering from identified diseases. This computer data base is preferably used in conjunction with integrated neural network analysis software in order to match fluorophore assisted carbohydrate electrophoresis banding patterns from patients with the data base comprising numerous known standards. Improving the information in the fluorphore assisted carbohydrate electrophoresis banding data base serves to increase the accuracy of diagnoses made by the neural network.

The subject invention provides a number of advantages over conventional techniques for diagnosing disease conditions that manifest themselves in part through changes in diagnostic carbohydrate concentrations. The present invention permits the simultaneous measurement of diagnostic carbohydrate quantities in multiple samples. Moreover, diagnostic carbohydrates specific for several diseases may be analyzed simultaneously. Another advantage of the present invention is the ability to detect carbohydrate metabolism diseases without the need to assay the activity of the defective enzyme in the patient. Furthermore, the subject invention permits the identification of the structure of carbohydrates that accumulate in the course of the disease. Additionally, the subject invention may be used to ensure diagnostic carbohydrate levels for carbohydrates that are chemically uncharacterized since there is no need to produce high specific reagents. A further advantage of the subject invention is the high sensitivity of the detection system.

The invention having been described, the following examples are offered to illustrate the subject invention by way of illustration, not by way of limitation.

EXAMPLES

Performing Fluorophore Assisted Carbohydrate Electrophoresis

Approximately 100 microliters of patient urine is partially purified using a centrifugal concentrator, such as the Millipore Ultra Free Device, to remove the high molecular weight compounds in the urine. The sample is then placed in a microcentrifuge tube and dried using a centrifugal vacuum evaporator centrifuge vacuum evaporator. To each dried sample is added 5 $\mu$l of 0.2M aminonapthalene-1, 3, 6-trisulphonic acid (ANTS) solution in acetic acid/water (3:17 v/v) and 5 $\mu$l of 1.0M NaCNBH$_3$ solution in dimethyl sulphoxide (DMSO). The solution is vortex mixed, centrifuged at 10,000 g to ensure all the reactants are in the tips of the tubes, and incubated at 37° C. for 15 h. The reaction mixture is dried under vacuum for 4 h in a centrifuge vacuum evaporator at approximately 45° C. and dissolved in a suitable concentration of electrophoresis sample buffer, so that the concentration of each labelled saccharide was 100 pmol/ul.

The labelled samples are subjected to polyacrylamide gel electrophoresis using a standard type electrophoresis apparatus, such as that from Hoefer Scientific Instruments. The electrophoretic buffer used is based on the Tris/HCl/glycine discontinuous system of Laemmli, but SDS is omitted throughout. The polyacrylamide gel consists of 35% (w/v) acrylamide containing 1% (w/v) NN'-methylenebisacrylamide respectively as a crosslinker. The polymerization of the gel is initiated by the addition of 20 ul of 10% (w/v) ammonium persulphate solution and 10 ul of NNN'N'-tetramethylene-diamene/12 ml of gel solution. The resolving gel size is 100 mm high×120 mm wide×approx. 0.3 mm thick. A stacking gel is used. The sample wells are 7 mm wide. Samples are electrophoresed at 2000V for 240 min until the buffer front reaches approximately 5–10 mm from the gel base. All voltages are held constant. The gels are cooled to 5–7° C. by the surrounding stirred lower electrode buffer.

The gel is photographed using a cooled CCD camera system, such as the Astromed CCD camera, see, U.S. Pat. No. 4,874,492, herein incorporated by reference. The gel is also photographed after removal from its cassette and placed on a U.V. light box (such as a Transilluminator, type TM 40) with a maximum emission wavelength of 302 nm and a power of approximately 700 uW/cm$^2$. A Polaroid type 55 film (ISO 50), which gives both a negative and a positive photograph, a Wratten 8 gelatin filter (Kodak), an aperture of f4.5 and an exposure time of 50 s are used.

Diagnosis of Glycoconjugate Metabolic Diseases

Urine samples from patients suffering from sialidosis, mannosidosis, $GM_1$ gangliosidosis, and Moriquo A disease were obtained. The urine samples from the patients and from 2 healthy individuals were labeled with aminonapthalene-1, 3, 6-trisulphonic acid (ANTS) and subjected to electrophoresis as described above.

The carbohydrate band patterns produced by the patient samples could be distinguished from one another and could also be distinguished from the pattern produced from the urine obtained from healthy individuals.

Use of Carbohydrate-Modifying Enzymes in Diagnosis of Lysosomal Storage Diseases Urine samples were obtained from normal individuals and patients suffering from the lysosomal storage diseases fucosidosis and mannosidosis. Urine samples were split into different aliquots. Fucosidase and jack bean α-mannosidase were added separately to individual aliquots of urine samples. The enzyme containing samples were subsequently incubated to permit the enzyme catalyzed reaction to progress. The carbohydrates in the urine sample were then labelled with amino naphthalene-1,3,6-trisulphonic acid (ANTS), essentially as described in the previous examples. Carbohydrates in the ANTS labelled urine samples from normal individuals, and untreated samples from patients suffering from the lysosomal storage diseases, and enzyme treated urine samples from the patients were analyzed by fluorophore assisted carbohydrate electrophoresis. A standard carbohydrate mixture was also run simultaneously in order to provide additional gel migration standards. Comparison of the fucosidosis patient urine samples between the fucosidase treated and untreated samples revealed significant changes in the observed banding pattern, with the disappearance of many of the most prominent bands seen in the untreated fucosidosis patient sample. Similarly, when comparing the urine samples of mannosidosis patients that were treated with mannosidase with the untreated portions, many of the prominent bands seen in the untreated mannosidosis were seen to disappear in the mannosidase treated sample. The fluorophore assisted carbohydrate electrophoresis results were recorded by a CCD scanning system and analyzed using computer image analysis software to compare the banding patterns of the different samples.

The foregoing written specification is considered to be sufficient to enable one skilled in the art to practice the invention. Indeed, various modifications of the above-described modes for carrying out the invention which are obvious to those skilled in the field of clinical chemistry or related fields are intended to be within the scope of the following claims.

I claim:
1. A kit for the diagnosis of a disease characterized by altered levels of a diagnostic carbohydrate present in a sample containing a mixture of carbohydrates, said kit comprising,
  (a) a labeling dye suitable for labeling a carbohydrate,
  (b) a labeling reducing agent capable of labeling said carbohydrate with said labeling dye,
  (c) a carbohydrate standard for gel electrophoresis suitable for measuring the quantity of at least one diagnostic carbohydrate in said sample; and
  (d) a database in a computer readable form said database comprising information describing the fluorophore-assisted carbohydrate electrophoresis banding patterns of patients suffering from diseases that produce changes in diagnostic carbohydrate levels.

2. A kit for the diagnosis of a disease characterized by altered levels of a diagnostic carbohydrate present in a sample containing a mixture of carbohydrates, said kit comprising:
  (a) a labeling dye suitable for labeling a carbohydrate, wherein said labeling dye is selected from the group consisting of 8-amino-1,3,6-naphthalene trisulfonic acid, 1-amino-6,8-disulphonic acid, lucifer yellow, and 2-aminoacridone,
  (b) a labeling reducing agent capable of labeling said carbohydrate with said labeling dye; and
  (c) a carbohydrate standard for gel electrophoresis suitable for measuring the quantity of at least one diagnostic carbohydrate in said sample.

3. The kit of claim 2 wherein said labeling reducing agent is a cyanoborohydride.

4. The kit of claim 3 wherein said kit further comprises a reagent mixture for the generation of a polyacrylamide gel suitable for the separation of carbohydrate mixtures comprised in said carbohydrate standards and in a suitable patient sample.

5. The kit of claim 2 wherein said kit further comprises a carbohydrate modifying catalyst.

6. The kit of claim 5 wherein the carbohydrate-modifying catalyst is selected from the group consisting of hydrolase, lysase, acetylase, sulfatase, phosphatase, kinase, epimerase, methylase, amidase, transferase, lectin, and antibodies.

7. The kit of claim 1 or 2 wherein said carbohydrate standard of item (c) is capable of measuring altered levels of diagnostic carbohydrates associated with a Lysosomal Storage Disease.

8. The kit of claim 7 wherein said kit further comprises a carbohydrate modifying catalyst.

9. The kit of claim 8 wherein the carbohydrate-modifying catalyst is selected from the group consisting of hydrolase, lysase, acetylase, sulfatase, phosphatase, kinase, epimerase, methylase, amidase, transferase, lectin, and antibodies.

10. The kit of claim 1 or 2 wherein said carbohydrate standard of item (c) is capable of measuring altered levels of diagnostic carbohydrates associated with a disease selected from the group consisting of Fucosidosis, Mannosidosis, Sialidosis, GM1 Gangliosidosis, Gaucher Disease, Sandhoff Disease, and Moriquo A Disease.

11. The kit of claim 2, said kit further comprising:
  a database in a computer readable form, said data base comprising information describing the fluorophore-assisted carbohydrate electrophoresis banding patterns of patients suffering from disease that produce changes in diagnostic carbohydrate levels.

12. The kit of claim 11 wherein said labeling reducing agent is a cyanoborohydride.

13. The kit of claim 11 wherein said kit further comprises a reagent mixture for the generation of a polyacrylamide gel suitable for the separation of carbohydrate mixtures comprised in said carbohydrate standards and in a suitable patient sample.

14. The kit of claim 1 or 2 wherein said standard comprises a mixture of at least two different carbohydrates.

* * * * *